(12) United States Patent
Barstis et al.

(10) Patent No.: US 10,119,981 B2
(45) Date of Patent: *Nov. 6, 2018

(54) ANALYTICAL DEVICES FOR DETECTION OF LOW-QUALITY PHARMACEUTICALS

(71) Applicant: St. Mary's College, Notre Dame, IN (US)

(72) Inventors: Toni L. O. Barstis, Niles, MI (US); Mary M. Bevilacqua, Boulder, CO (US)

(73) Assignee: St. Mary's College, Notre Dame, IN (US)

(*) Notice: Subject to any disclaimer, the term of this patent is extended or adjusted under 35 U.S.C. 154(b) by 154 days.

This patent is subject to a terminal disclaimer.

(21) Appl. No.: 15/254,186

(22) Filed: Sep. 1, 2016

(65) Prior Publication Data

US 2016/0370389 A1    Dec. 22, 2016

Related U.S. Application Data

(63) Continuation-in-part of application No. 13/829,753, filed on Mar. 14, 2013, now Pat. No. 9,557,274.

(60) Provisional application No. 61/684,570, filed on Aug. 17, 2012.

(51) Int. Cl.
*G01N 33/94* (2006.01)
*G01N 21/78* (2006.01)
*G01N 21/84* (2006.01)

(52) U.S. Cl.
CPC ......... *G01N 33/9446* (2013.01); *G01N 21/78* (2013.01); *G01N 21/8483* (2013.01); *G01N 33/94* (2013.01); *Y10T 436/11* (2015.01)

(58) Field of Classification Search
CPC ........... G01N 33/9446; G01N 21/8483; G01N 21/78; G01N 33/94; Y10T 436/11
See application file for complete search history.

(56) References Cited

U.S. PATENT DOCUMENTS

| 6,136,549 | A  | 10/2000 | Feistel |
| 6,770,487 | B2 | 8/2004  | Crosby |
| 6,847,451 | B2 | 1/2005  | Pugh |
| 7,344,081 | B2 | 3/2008  | Tseng |
| 7,885,444 | B2 | 2/2011  | Wang |
| 2008/0012083 | A1 | 1/2008 | Gilton |
| 2011/0111517 | A1 | 5/2011 | Siegel et al. |

(Continued)

OTHER PUBLICATIONS

Li et al., "A perspective on paper-based microfluidics: Current status and future trends", Biomicrofluidics, 2012, v. 6, pp. 011301-1-011301-13.

*Primary Examiner* — Samuel P Siefke
(74) *Attorney, Agent, or Firm* — Winston & Strawn LLP

(57) ABSTRACT

A multilayer Paper Analytical Device (PAD) and method for detection of a low quality pharmaceutical or dietary supplement product. The multilayer PAD includes one or more assay regions, one or more reagent vessels in registry with the assay region(s), and a non-chemically interfering binder agent disposed between the assay regions and vessels, so that rupture of the vessels enables the reagents to wet the assaying regions and contact a sample of a suspected low quality pharmaceutical product or dietary supplement for testing thereof. A kit is also provided for detection of a low quality pharmaceutical or dietary supplement product, the kit including a multilayer PAD and instructions for using the kit.

19 Claims, 3 Drawing Sheets

(56) References Cited

U.S. PATENT DOCUMENTS

2011/0189786 A1    8/2011   Reches et al.
2012/0178176 A1    7/2012   Haas et al.

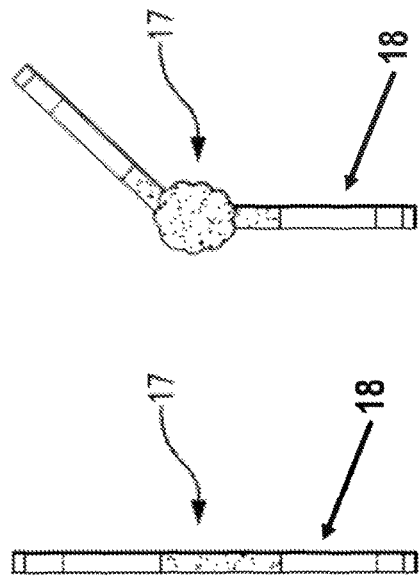
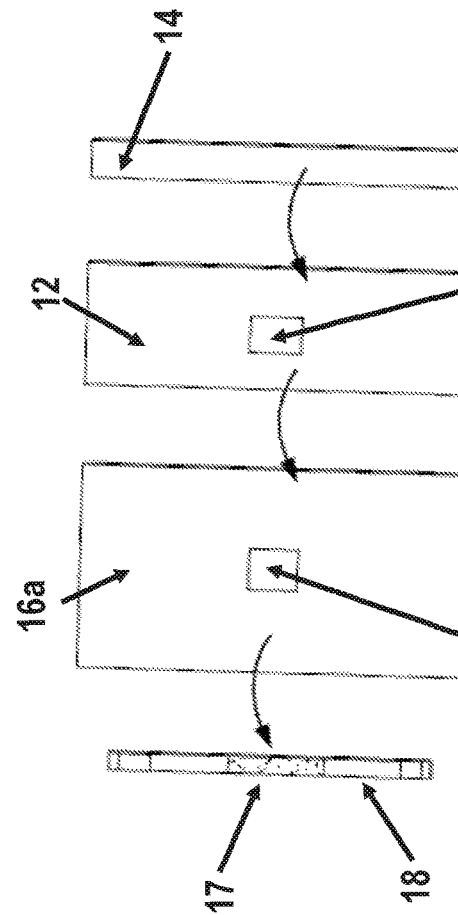
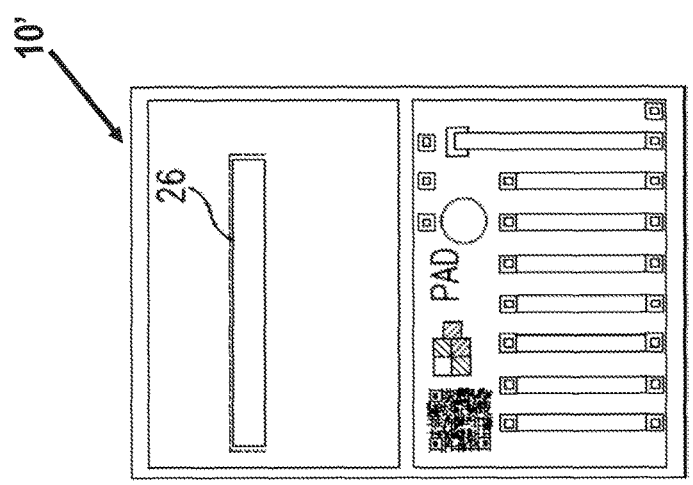

ANALYTICAL DEVICES FOR DETECTION OF LOW-QUALITY PHARMACEUTICALS

CROSS REFERENCE TO RELATED APPLICATIONS

This application is a continuation-in-part of application Ser. No. 13/829,753 filed Mar. 14, 2013, which claims the benefit of application No. 61/684,570 filed Aug. 17, 2012, the entire content of each of which is expressly incorporated herein by reference thereto.

FIELD OF THE INVENTION

The invention relates to user-friendly analytical devices, in particular, Paper Analytical Devices (PADs), for detection of at least two chemical components indicative of a low quality pharmaceutical product or dietary supplement, and a method of use thereof.

BACKGROUND OF THE INVENTION

User-friendly analytical devices such as Paper Analytical Devices (PADs) are known in the art as convenient and inexpensive means for assaying chemicals. As these devices contain all necessary reagents and do not require power, they are easy to operate in a field setting. U.S. Pat. No. 6,136,549 discloses systems for conducting spectrophotometric analysis which includes a chromatographic medium, such as an assay test strip, that is designed to be contacted with a test solution having activated magnetic particles. U.S. Pat. No. 6,770,487 discloses "dip stick" style paper-based diagnostic test devices, in which identifying information and the test result are machine-readable. U.S. Pat. No. 6,847,451 discloses apparatuses for determining the concentration of an analyte in a physiological sample, which include at least one light source, a detector array, means for determining whether a sufficient amount of sample is present on each of the plurality of different areas, and means for determining the concentration of the analyte based on the reflected light detected from those areas determined to have sufficient sample. U.S. Pat. No. 7,344,081 discloses a method of automatically detecting a test result of a probe zone of a test strip comprising capturing an image of a one-dimensional bar code and an image of at least one test strip from a scanning object, and determining a setting value for the at least one test strip based, at least in part, on said captured image of said bar code. U.S. Pat. No. 7,885,444 discloses a method for determining a response of each probe zone on a test strip by selecting an average pixel value of each section of reference white respectively adjacent to the image of a target line to serve as a reference for determining a color response of the target line. US Publication No. 2008/0012083 discloses an analytical system-on-a-chip that can be used as an analytical imaging device, for example, for detecting the presence of a chemical compound, which may also include software that can detect and analyze the output signals of the device. US Publication No. 2011/0189786 discloses a method of detecting the presence or absence of an analyte in a fluid sample. The method includes applying the sample to an inlet zone of a diagnostic system that includes a hydrophilic cotton loading thread to serve as a capillary to deliver a solute to a reagent testing zone, and detecting color change of reagent analyte interaction. US Publication No. 2011/0111517 discloses a paper-based microfluidic assay device comprising a porous, hydrophilic substrate; a fluid-impermeable barrier defining a boundary of an assay region and a boundary of a main channel region, the main channel region fluidically connected to the assay region; and a strip of conductive material disposed on the porous, hydrophilic substrate for detecting the concentration/flow of analyte. In a commercial embodiment, pSiFlow Technology Inc. provides a mobile testing and process management web infrastructure built around its Calibrated Color Match (CCM) image processing technology that enables digital reading of color-based test strips using any mobile phone with a camera.

The World Health Organization (WHO) reports that many medications for sale in underdeveloped countries are of low quality, which either contain low concentrations of active ingredients that are not sufficient to treat the underlying condition, or contain substitute active ingredients that may have adverse effects on some patients, or have no active ingredients at all; or even contain toxic ingredients. Although the prevalence of such medications is difficult to measure, both the WHO and US Food and Drug Administration (FDA) estimate that 10-30% of all drugs in the developing world are low quality drugs. A consumer taking a low quality pharmaceutical product may die or experience other adverse medical effects from the underlying condition or from contaminants in the pharmaceutical product. The failure of treatment may be mistaken for resistant strains of the disease requiring much more rigorous treatment that can itself endanger the patient. Also, low quality medications that fail to cure the underlying condition may speed up development of actual resistance in pathogens.

Multiple factors contribute to the prevalence of low quality pharmaceutical products in developing countries. First of all, manufacturing and selling low quality pharmaceutical products are both easy and hugely lucrative, and low quality products can enter the supply chain at many points. Moreover, buyers and consumers cannot assess identity or quality of pharmaceutical products. Furthermore, manufacturing low quality pharmaceutical products is not a serious crime in many countries, and there is a low risk of detection from official agencies and organizations. Finally, the time, expertise, and expense required for testing pharmaceutical products is a particular barrier to effective post-market surveillance of pharmaceuticals in developing countries.

Some medical conditions arise not from a pathogen, but from a deficiency in an essential nutrient. For example, widespread iodine deficiency is a problem in many underdeveloped countries that is associated with developmental impairment in children. Fortification of table salt with potassium iodate or potassium iodide is a common route to address this problem. However, production and distribution methods for iodized table salt in many developing countries yield inadequate or inconsistent levels of iodine. Unfortunately, the time and expense of testing for iodized table salt deters manufacturers, distributors, and end-users from testing iodized table salt to determine iodine concentrations. Thus, a low-cost method of testing iodized table salt at the production facility or in the field is needed to determine whether the salt is adequately fortified with iodine within therapeutic concentrations recommended by the WHO.

Thus, there exist long-felt needs for a low-cost, easy-to-use, reliable, minimalistic chemical means of detecting low quality pharmaceutical products and dietary supplements such as iodized salt. These quality problems are also present for veterinary medications and nutritional supplements for animals. The present invention addresses these needs by providing an inexpensive, user-friendly, consistent analytical device capable of detecting various low quality pharmaceutical products and measuring levels of iodine in iodized salt.

SUMMARY OF THE INVENTION

The present invention provides an easy-to-use, inexpensive analytical device, typically a Paper Analytical Device (PAD), for detection or analysis of a low quality pharmaceutical product or dietary supplement. The PAD comprises one or more assay regions; one or more vessels each having a wall that houses one or more reagents in registry with at least one assay region for which testing for a chemical component is desired; and a non-chemically interfering binder agent disposed between the assay regions and vessels. The vessels are arranged to be adjacent to the assaying regions with the binding agent configured for providing a fluid path such that rupture of a vessel wall establishes fluid communication between the one or more reagents released by the ruptured vessel wall and the corresponding assay region along the fluid path.

Each assay region is configured to receive a sample of a suspected a low quality pharmaceutical product or dietary supplement such that, after activation of the device by rupturing of a vessel wall in registry with the assay region, the reagent wets the assaying region for reaction with the sample.

The at least one vessel is fabricated from a rupturable material and the device may also include a hydrophobic material in the form of a sheet that is adjacent each vessel and that has openings that forms part of the fluid path for each vessel. The binder agent is preferably parafilm or other suitable adhesive for joining the components together. The assaying region advantageously comprises a hydrophilic substrate and is adhered to the plastic sheet of the hydrophobic material by the parafilm, with the parafilm having an opening which is in alignment with the opening of the hydrophobic material sheet to assist in forming the fluid path between the vessel and the assaying region.

The hydrophobic material is preferably part of a lamination that surrounds the one or more vessels to contain therein any fluid which does not flow to the assaying region and the assaying regions are attached to an outer surface of the plastic sheet. The device further comprises an informational substrate that is associated with the PAD in a visible position thereon. The informational substrate may be present within the lamination in order to be isolated from the vessels.

In another embodiment, the PAD can be used for detection or analysis of at least two chemical components in a dosage formulation indicative of a low quality pharmaceutical product or dietary supplement. The analytical device typically comprises a multilayer PAD having one or more assay regions of porous, hydrophilic material in communication with a non-chemically interfering binder agent such as parafilm disposed adjacent at least to a reference card or hydrophobic layer or between both. Vessels containing reagents are in registry with at least one assay region of the hydrophilic material for which testing for a chemical component is desired. Rupture of a vessel wall establishes communication between corresponding assay regions and the reagent released by the ruptured vessel wall.

Preferably, the binding agent and, when present, the hydrophobic layer provide a fluid path such that rupture of a vessel wall establishes fluid communication between the one or more reagents released by the ruptured vessel wall and the corresponding assay region along the fluid path. Also, each assay region is configured to receive a sample of a suspected a low quality pharmaceutical product or dietary supplement such that, after activation of the device by rupturing of a vessel wall in registry with the assay region, the reagent wets the assaying region for reaction with the sample.

The vessel may be a separable tubular member insertable between two layers of the PAD. In this exemplary embodiment, the vessel wall is fabricated from a frangible material. Alternatively, the vessel may be integrally formed within the PAD, with the vessel wall including a rupture zone. Additionally, the vessels may be adhered to the hydrophilic material that contains the assaying regions byt a binder material of a suitable adhesive of parafilm or other thermoplastic or moisture resistant adhesive that can join paper to glass or plastic. The one or more vessels when ruptured are preferably in fluid communication with the assay region, e.g., by direct contact, or by a channel forming or defining a fluid path or by another structure joining the two so that rupture of the vessel wall releases the reagent which is then directed to the assaying region. A porous, hydrophilic substrate such as a paper may be used for the assay regions. The device includes at least one or more of an information identification zone and a color calibration zone. Alternatively, at least one or more of the information identification zone and the color calibration zone may be integrated within the hydrophobic layer or layers. The informational substrate may further include at least one electronically readable information zone that, after activation of the device, provides color information necessary for detection of the chemical components. The electronically readable information zone comprises alignment references for transforming or correcting a captured image of the PAD to facilitate analysis and processing of the color information to more accurately detect the at least two chemical components. The alignment references include a plurality of fiducial markers for orienting the captured image. These zones can be provided on the hydrophilic material that also includes the assay regions or they can be provided on a separate card or substrate that is provided on or in the PAD. There is no restriction on where these zones appear as long as they are visible for viewing and processing of the PAD after the reagents are released and the sample testing is complete.

The chemical components to be detected by the whole PAD include at least one active ingredient and possibly one or more excipients. The active ingredient includes at least one of an anti-malarial, antibiotic, anti-parasitic, cox-inhibitor, analgesic, antipyretic, phosphodiesterase-5 inhibitors, anti-viral, anti-cancer or dietary supplement compound. The color information determines whether an inappropriate combination of active ingredient and excipient is present, indicative of a low quality pharmaceutical or dietary supplement product. The PAD disclosed and shown herein is also readily used for analyzing the quality of a pharmaceutical or nutritional product, such as an iodized table salt.

Also provided is a method for detection of a low quality pharmaceutical or dietary supplement product. The method comprises providing the multilayer analytical device as disclosed herein and disposing the product to be analyzed into assay regions in order to detect certain chemical components of the pharmaceutical or dietary supplement product. The device is activated in a manner such that the reagents contact the product to be analyzed in the assay regions to provide color information. In some cases, vessel rupture may establish communication between a reagent and the corresponding assay region. Generally, the activating of the device includes rupturing of the vessel wall sufficiently to enable release of the reagents therein onto the assay regions. The subsequently developed color information is analyzed to detect the presence or absence of the chemical components.

Additionally, a kit may be provided for detection of a low quality pharmaceutical or dietary supplement product. The kit comprises, but is not limited to, a multilayer analytical device as disclosed herein and instructions for using the kit. The instructions include at least instructions for detecting the presence or absence of the at least two chemical components indicative of a low quality pharmaceutical product or dietary supplement using the kit. The instructions may be provided in hard copy, accessible via a link to a website or mobile application, accessible via a QR code or any combination thereof (including any equivalent and complementary instruction formats). The kit may also include a solvent that is present in an amount sufficient to dilute the pharmaceutical product to be analyzed to an analyzable concentration.

The PAD as described and shown herein may be provided in singular or plural quantities and may also be provided with one or more other PAD configurations, including, but not limited, to those PAD devices described and shown in co-owned U.S. patent application Ser. No. 13/566,915, the entire content of which is expressly incorporated herein by reference thereto. Thus, the device can includes one or more additional assaying regions that contain dry reagents that are activated by the separate addition of a solvent to conduct further testing of a sample of the product.

BRIEF DESCRIPTION OF THE DRAWINGS

Further features of the invention, its nature and various advantages will be more apparent from the following detailed description, taken in conjunction with the accompanying drawings in which like reference characters refer to like parts throughout and in which:

FIG. 2 shows a front view of an exemplary multilayer paper analytical device (PAD) that is similar to that of FIG. 1 but that includes a grate for grinding samples with the PAD located within the lower rectangular region.

FIGS. 3 and 3A respectively show operation and assembly of the exemplary multilayer paper analytical device of FIG. 1, including the arrangement and placement of the vessels 18 which are located behind the assay regions of the test strips 14, so that when reagent 17 is released from the vessels 18 the assay regions of the test strips 14 are properly wetted.

DETAILED DESCRIPTION OF THE PREFERRED EMBODIMENTS

Figure 1:
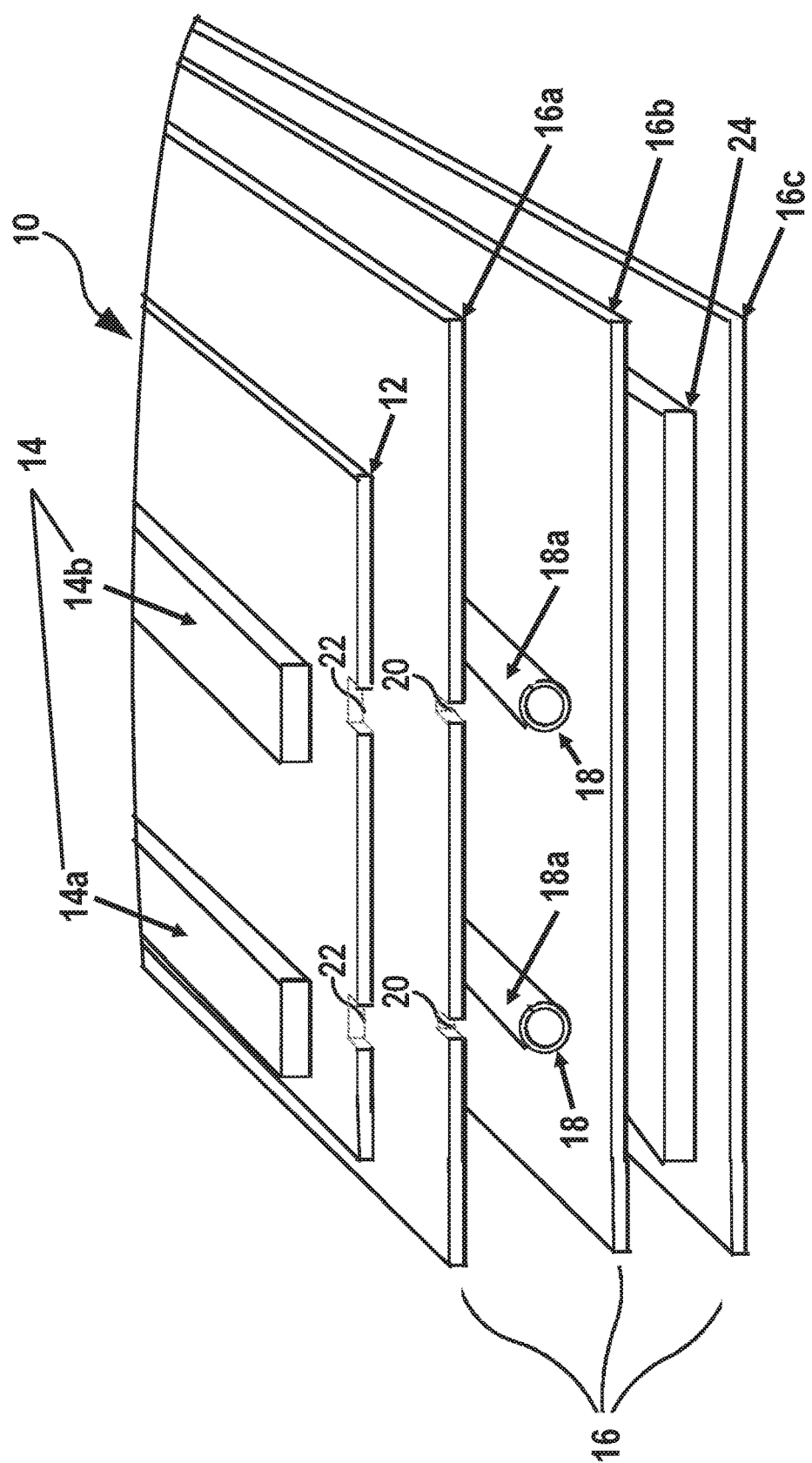
FIG. 1 shows an exploded cross-sectional view of an exemplary multilayer paper analytical device (PAD) to illustrate the arrangement of the PAD components in the device.

As used herein, "paper analytical device" (or "PAD") refers to a composition based on a porous hydrophilic material (such as paper) and comprising areas of hydrophobic barriers which define hydrophilic assay areas. The hydrophilic assay areas may include test reagents.

As used herein, "low quality pharmaceutical product" and "dietary supplement product" refers to products purported to be genuine products for treating a disease or disorder or providing a nutritional supplement but containing low concentrations of active ingredients that are not sufficient to treat purported use, a product containing substitute active ingredients that may have undesired side effects compared to the stated drug, a product containing active ingredients that have undergone degradation, or a product having no active ingredients at all. In addition, these terms include products that contain ingredients that should not be present in a genuine product of the stated type including ingredients that may be toxic.

As used herein, "active agent" refers to a chemical capable of being detected by an analytical device as disclosed herein, such as a PAD. The active agent may include chemically active ingredients, excipients or anticipated degradation products within a pharmaceutical formulation.

As used herein, a "camera device" refers to a device that contains a camera component. Exemplary camera devices are various types of digital cameras and scanners as well as mobile devices such as cell phones, smartphones or similar devices. When digital cameras are used, the images will be uploaded to a computer or other electronic device that is capable of transmitting the pictures to another location. Of course, when a picture or image is taken from a mobile phone, the phone already generally has the ability to forward the image, e.g., as a text message or as part of an e-mail.

The present invention provides an easy-to-use, inexpensive analytical device, such as a PAD, for detection of specific chemicals and/or chemical groups in an active ingredient, which is particularly capable of detecting various low quality pharmaceutical and dietary supplement products. One advantage of the present invention is that more than one active ingredient can be analyzed with the same device, which is especially useful in analyzing a combination drug. Moreover, in addition to verification of an appropriate active ingredient that should be present, it is also possible to screen for binders and fillers that should be present in the stated formulation, e.g., starch as a binder in acetaminophen tablets; and additionally, to screen for a multitude of likely substitute drugs, e.g., an antipyretic in place of expensive anti-malarial drugs, ampicillin in place of erythromycin, and binders or fillers such as gypsum or lactose in place of an active pharmaceutical.

Porous Hydrophilic Substrate

Typically, the analytical device of the invention comprises a porous, hydrophilic medium, preferably a paper such as a fast chromatography paper or an absorbant blotting paper. A suitable porous hydrophilic medium includes one that has a fast flow rate via capillary action, has enough absorption capacity to hold adequate amounts of reagent; has durability and stability such that it does not fall apart or fall over when wet; and is compatible with at least one of the methods used to fashion assay regions. Characteristics which should be considered when designing an analytical device of the invention, such as a PAD, include density, thickness, pH, basis weight, solvent flow-rate through fabricated substrate, compatibility with fabrication methods, pore size, and porosity. Examples of suitable materials for an analytical device of the invention, such as a PAD, include, but are not limited to nitrocellulose acetate, chromatography paper, cellulose acetate, cellulosic paper, filter paper, tissue paper, writing paper, paper towel, cloth, and porous polymer film. In one embodiment, the substrate for a PAD is Whatman 3MM Chr chromatography paper, Ahlstrom 205, Ahlstrom 222, Ahlstrom 226, Ahlstrom 319, or Whatman No. 1 filter paper. In one preferred embodiment, Ahlstrom 319 filter paper is used.

The medium may be provided as a sheet with appropriate lines or other demarcations of lanes for assaying of the samples and reagents that are received therein, or they can be provided as paper strips or tracks that are placed in alignment with or even in contact with the vessels. The medium or strips are adhered to the vessels or more typically, to a hydrophobic layer that is placed between the hydrophilic layer and the vessels. The medium or strips of the hydrophilic layer can be adhered to the hydrophobic layer by the binding agent which as noted preferably is parafilm. Other binding agents include adhesives that are capable of bonding paper to glass or plastic. The binding agent may comprise a thermoplastic adhesive that is the form of a film. Any adhesive that has some resistance to chemicals and that can bond paper to plastic would be suitable. Double sided adhesive tape can also be used. And the binding agent can be in the form or a sheet or strip but when in the form of a liquid can be deposited in a line or as drops.

The importance of the bonding agent is that is used to fix the position of the tubes in the PAD, such as upon the reference card or within the laminate. If the capillaries are not contained, then they move too freely and may not properly line up with the assaying regions where the colorimetric chemistry will take place between the reagents and the sample to be tested. Adhesing the paper assaying regions to the tubes minimizes this issue even if the tubes do move because the assaying regions are affixed directly to the tubes. In other embodiments the biding agent adheres the assaying regions to a hydrophobic layer or laminate that the holes or openings that provide a fluid path from the vessels to the assaying regions so that when the vessels are ruptured, the liquid reagents flow onto the assaying region for reaction with the sample.

Fabrication of the PAD and Assay Regions Thereupon

The final dimension of the PAD can have a length "L", width "W" and height or depth "H" that can vary, depending on the number and size of assay regions and information zones needed on the PAD. The height or depth is determined by the chemistry required to detect various components of a particular low-quality pharmaceutical or dietary supplement product.

Several assay regions are defined on the analytical device of the invention, either by affixing individual strips or other shapes cut from paper onto an inert backing material that has adhesive properties, or by patterning a piece of paper with a hydrophobic barrier substantially permeating the thickness of the paper medium to define the boundaries of the desired assay regions. The hydrophilic assay regions or reaction areas with the boundaries defined by the hydrophobic area can be in any suitable size or shape. The precise dimensions of the assay regions are determined by the type of reaction to be performed within each assay region, or for optimizing viewing results. Suitable shapes for reaction areas include rectangular lanes, circles (or "spots"), stars, squares, triangles, etc. Reaction areas can comprise multiple shapes. For example, a rectangular lane may culminate with a circle. The diameter of each circle can range from about 1.5 cm to about 0.3 cm. Preferably the circles are about 1.0 cm in diameter. The length of rectangular lanes can range from about 1 cm to the full length of the PAD, and the width can range from about 0.1 cm to the full width of the PAD.

The assay regions of the PAD can be produced in a number of ways that are known to one skilled in the art. For example, photolithography of a resist such as SU-8 can be used to produce hydrophobic regions within the hydrophilic paper medium according to the procedures laid out in US Publication No. 2011/0111517 A1, which is herein incorporated in its entirety. Alternately, the PAD can be fabricated using wax printing according to the procedures laid out in Lu, Y.; Shi, W.; Jiang, L.; Qin, J.; Lin, B. *Electrophoresis* 2009, 30, p. 1497-1500 and Carrilho, E.; Martinez, A. W.; Whitesides, G. M. *Anal. Chem.* 2009, 81, p. 7091-7095, which are herein incorporated in their entireties. In a preferred embodiment, an HP ColorQube printer is used to deposit wax ink, preferably black, in the desired regions of Ahlstrom 319 paper according to a template laid out in a computer program such as Adobe Illustrator; alternatively, the template may be stored and printed as an image file such as a PDF. The preferred paper type is too thick for wax deposition on one side of the paper to form the necessary continuous hydrophobic barrier, so wax ink must be printed on both sides of the paper, after which the paper is heated to 70-120° C. (preferably 100° C.) to allow the wax to melt through the paper and form a continuous hydrophobic barrier surrounding the desired assay region. For prototyping, a wax crayon can be applied heavily around the regions desired on both the front and back of the paper, after which the paper is heated to 70-120° C. (preferably 100° C.) to allow the wax to melt through the paper and form a continuous hydrophobic barrier surrounding the desired assay region.

The "cut and paste" method requires the lanes to the cut from the hydrophilic paper medium and adhered to a relatively strong backing, mylar plastic for example, using an adhesive. This method does not require the application of a hydrophobic agent in order to define the hydrophilic reaction areas. As a result, the chance of bleed-over of hydrophobic agent into the lanes is eliminated. The lanes can be cut using any precise cutter, such as an exacto-knife or craft cutter.

Referring to FIG. 1, an exemplary device 10 that employs the "cut and paste" method is shown as a multilayer device employing a non-chemically interfering binder agent such as parafilm 12 to attach unadulterated test strips 14 (shown as 14a and 14b) to the last one laminate backing 16 (as shown herein, parafilm 12 attaches test strips 14a and 14b to first laminate backing 16a), such as by placing the parafilm 12 on the upper side of the laminate backing 16a then placing the test strips (14a and 14b) on the upper side of the parafilm 12. One or more vessels 18 are disposed between first and second laminate backings 16a and 16b with each vessel having a wall 18a for containment of an unstable or corrosive reagent 17 therein. The laminate materials are clear plastic sheets that are sealed around the border where the sheets are in contact with each other. FIG. 2 illustrates this border. Sealing the edges of the backings provides compartments which can retain the vessels therein and separately a substrate that includes other important information as discussed herein.

FIGS. 3 and 3A illustrate the vessel 18 before and after being ruptured which releases the reagent 17 into the assay region of the test strip 14 for testing of chemical components. The objects in FIG. 3A are illustrated from left to right in the order of a vessel 18 containing reagent 17, a laminate backing 16a (a hydrophobic layer) that has a release opening 20, a parafilm 12 (or other non-chemically interfering binder agent) that also has a release opening 22, and a test strip containing assay regions 14. Since release openings 20 and 22 are in registry (aligned) with the assay regions of test strips 14, upon rupturing vessel 18, reagent 17 flows along a fluid path through a release opening 20 of a laminate backing 16a and a release opening 22 of a parafilm 12 to reach assay regions of test strips 14. Vessels 18 may be independent tubular members as shown that are placed in registry with release openings 20 provided in first laminate backing 16a and in further registry with corresponding release openings 22 in parafilm 12. Release openings 20 and 22 are in registry with those test strips 14 for which testing for a particular chemical compound and/or active agent is desired. For example, test strip 14a may be employed for detecting acetaminophen or vitamin C, while test strip 14b may be employed for detecting starch or vitamin C. Several layers of the laminate backings (such as 16a, 16b and 16c in FIG. 1) are preferably sealed by lamination at their borders to form a sealed pouch that contains the vessels therein. The vessels are preferably retained in one compartment which the substrate 24 is provided in a separate compartment. FIG. 2 shows the sealed border of the laminate with the substrate 24 appearing in an upper compartment along with a grate for abrading the drug sample while the vessels and assaying regions are arranged in the lower part of the PAD with the vessels placed within the laminate and secured in position in alignment with the assaying regions of the paper strips. During use, the released liquid reagents are drawn to the paper through the fluid paths so that the paper can be wetted for reaction with the drug sample thereon.

The substrate 24 may be a paper layout may be provided between second laminate backing 16b and a third laminate backing 16c, which paper layout includes at least one or more of at least one information identification zone (e.g., at least one electronically readable information zone such as a bar code, QR code or set of fiducial marks) and at least one color calibration zone that are readily observed during use of the device. The information identification zone contains information about the PAD-type, serial number and fabrication date and allows for remote identification of the PAD. The color calibration zone allows for accurate computer analysis of PAD images taken under varying light conditions. Fiducial markers aid in orienting captured images so that an image software can correct or transform the captured image. It is understood that one or more of the information identification zone, the color calibration zone and the fiducial markers may be provided on any of the backings 16 and that these features may be incorporated on separate layers of device 10 to augment the interchangeability of the layers with one another (for example, providing substrate 24 with the fiducial markers and integrating the information identification and color calibration zones on one or more backings 16). The informational substrate 24 is preferably provided in a sealed portion of the laminate that is not in fluid contact with the vessels so that the information on the substrate 24 is not affected by the reagents that are released by the vessels for testing. Alternatively, the informational substrate 24 is made of a plastic material that is resistant to the reagents that are released from the vessels.

It is understood that laminate backings 16 are not limited to the quantity shown, and that fewer or additional laminate backings may be employed as may be amenable for successful testing of detectable chemicals and active agents. It is also understood that the layers shown herein are exemplary, and that the layers may be placed in any order amenable to the successful practice of the device.

Referring further to FIG. 2, a related device 10' employs the "cut and paste" method in which the vessels and test strips are integrated with a grate 26 on which a chemical or active agent (e.g., in the form of a pill) may be applied. Grate 26 may comprise emery paper, cardboard or any other suitable material or structure for deriving a suitable testing sample while ensuring a portable and easily stored device.

When vessels 18 are independent members insertable between laminate backings 16a and 16b and sealed therein, vessel wall 18a may be fabricated from a frangible composite or comparable or equivalent material. Although vessels 18 are shown herein as independently insertable members, it is understood that one or more vessels may be integrated with one or both of laminate backings 16a and/or 16b. For example, either laminate backing 16a or 16b may be fabricated to include a vessel integral therewith, thereby obviating the need for two laminate backings to house a vessel therebetween. In this example, release openings 20 may be replaced by frangible zones (not shown) that are in registry with release openings 22 in parafilm 12 and release reagent 17 upon rupture thereof. Also, one or more insertable vessels may be incorporated with one or more vessels integral with device 10, which may be desirable when testing of different chemicals will be conducted at different times and/or in different locations. Such a configuration may be desirable when employing different reagents having different storage properties.

Vessels 18 stably house those reagents which may degrade over time when exposed to ambient conditions, such that long-term storage is achieved. Referring further to FIGS. 3 and 3A, vessels 18 can be loaded with unstable or corrosive reagents (illustrated generally as reagent 17) that are readily released upon compromise of vessel wall 18a. Because vessels 18 are built into the PAD, they can be broken on-site to release the reagent as needed. Precise lane control as to test strips 14 is thereby maintained while ensuring device requiring minimal packaging and thereby minimal cost.

Reagents and Reagent Deposition

The analytical device also contains at least one assay reagent in each of the assay regions. In one embodiment, a hydrophobic barrier defines independent isolated assay regions of various shapes and at least one of the assay regions includes a reagent or precursor thereof that is capable of identifying a component that should not be present in the pharmaceutical product.

Various reagents or regent forming precursors can be optionally loaded into the reaction areas. The reagents or precursors can be loaded into the reaction area individually by hand, or via an automated process. The regents may be pre-loaded as liquid solutions or suspensions or may be loaded into the vessels. Examples of reagent materials suitable for use in the analytical device of invention such as a PAD include, but are not limited to, Folin-Ciocalteu, potassium hexacyanoferrate(II) trihydrate, iodine-potassium iodide reagent, universal indicator, ferric chloride, triiodide, triiodide-starch complex, soluble starch; cationic, anionic, and neutral pH indicators; barium chloride, sodium rhodizonate, potassium hexacyanoferrate(II), NaOH, tosic acid, potassium carbonate, citric acid, copper sulfate, sodium tetraphenylborate, cobalt thiocyanate, ammonium molybdate, nitroaniline, 1,2-napthaquinone-4-sulfonate, dimethylglyoxime, and paradimethylaminobenzaldehyde. These reagents may be deposited from aqueous solution or from organic solution. For wax printed PADs, acetonitrile is the preferred organic solvent because the wax barriers are not affected by the acetonitrile. Surprisingly, many colorimetric reagents plateau at particular concentrations so that adding additional reagents will not enhance color results. Thus, the upper limit on the amount of reagents added is more or less determined by the PAD's loading capacity. The volume of the reagent loaded onto the PAD can range from about 2 to about 100 microliters, or from about 10 to about 50 microliters, or preferably from about 20 to about 30 microliters.

Reagents may be deposited on the surface of the analytical device in many ways that will be familiar to those skilled in the art, including but not limited to the use of: microcapillary pipettes and droppers, single- or multi-channel automatic pipetting devices, rods that can capture a droplet of solution or "frog" type depositors that perform this function with multiple rods simultaneously, dipping or spraying equipment, or solution deposition robots.

General Method of Use

The invention also provides a method for detecting the presence or absence of a chemical and/or a chemical functional group in a composition, or for quantifying the amount of at least one chemical in a composition, or for comparing the amounts of two chemicals present in the composition. This method comprises providing a paper analytical device of the invention; disposing the composition into the assay region in a manner such that it contacts the assay reagent or reagents in the assay region; and analyzing the assay region to detect the presence or absence of the chemical and/or the chemical functional group in the composition or to detect the amount of the targeted chemical or chemicals present in e assay region or to compare the amounts of two chemicals present in the composition.

Compositions Suitable for Analysis

The chemicals to be detected can be in any suitable formulation, including tablets, pills, solids, or powders. Other suitable formulations include liquids, such as suspensions, syrups, or solutions of medications. In some instances, a solid formulation can be used directly with the PAD, by swiping or rubbing the formulation onto the PAD at a specific location(s). In other instances, a solid formulation must be diluted into a liquid solution or suspension in order to be used with the specific PAD. Liquid formulations may be added directly to the PAD, or may be further diluted and then added to the PAD. In some instances, a formulation may be used both directly and also as a dilution on the same PAD.

The PADS can be used to detect low quality human and animal pharmaceutical products, including classes of treating agents such as anti-malarials (artemether, lumifantrine), beta lactam antibiotics (ampicillin, amoxicillin), cox-inhibitors, anti-parasitic drugs (albendazole, mebendazole, iveiniectin), antipyretics (aspirin, acetaminophen) phosphodiesterase inhibitors (sildenafil citrate), and anti-virals (ostamilvir phosphate). They can also be used to analyze foodstuffs that have been supplemented or fortified with micronutrients (iodine, iron, zinc, vitamin C) or with medications (diethylcarbamazine citrate). However, other classes of active agents are also contemplated, such as NSAIDs (ibuprofen), analgesics (lidocaine), HMG-CoA reductase inhibitors (statins), ace-inhibitors (quinapril), macrolide antibiotics (erythromycin), anti-anxiety medications (alprazolam), hi-polar disorder and schizophrenia medications (olanzapine), anemia medications (epoetin alfa), and anti-retrovirals (abacavir), etc. Specific PADs and their application are disclosed herein.

Deposition of the Composition to be Analyzed on the PAD and Activation of the PAD Tests In one embodiment, a drug tablet may be broken in half and rubbed on the surface of the paper in the assay regions, or a rough surface such as a piece of wire or plastic mesh or sandpaper may be used to assist in forming powdered material on the assay regions. The rough surface in the form of a grate can be provided on the PAD as shown in FIG. 2, if desired. Alternatively, a solid formulation may be crushed or ground to powder, or a capsule containing powdered material may be opened, and the powder may be spread on the assay region using a paddle or spatula. Such deposition of solid material may be carried out with the aid of an assisting device, such as a plastic mesh or plate pierced with holes in regions that correspond to the locations of the assay regions. In order to deposit a controlled amount of the composition to be analyzed, a straight-edge may be drawn across the top surface of the assisting device to pack the composition within the holes of the assisting device, after which the assisting device is lifted from the PAD. The composition may be disposed within the assay region by placing a solution or suspension containing the composition drop-wise onto the desired region of the paper analytical device. Alternatively, the composition may be disposed within the assay region by dipping part of the PAD into the solution or suspension of the composition and allowing the composition to move into the assay region with the resulting capillary flow.

In the preferred embodiment, the pharmaceutical product is applied directly to the vessel rupture zones where communication with the reagents forms a solution. The remaining pharmaceutical product is diluted with solvent and dropped onto the other assay regions.

General Method of Analysis of the Test Results

Once the composition has been applied to the assay regions, the disposing of the solvent into the assay regions typically causes a colorimetric change in each region that can be analyzed to detect the presence/absence of the chemical and/or the chemical functional group in the composition, to quantify the amount of the targeted chemical, or to compare the amounts of two chemicals present in the composition.

The hydrophobic regions can also define control regions within the hydrophilic paper medium. For example, a timer region may be included in order to alert the user when the test has completed. The timer region may comprise a color-generating reaction in which one component travels up the lane with the solvent flow and creates a color when it encounters another component at the top of the lane, or it may comprise other timing mechanisms such as delay of the solvent flow by a deposited reagent such as sugars, surfactants, or polymers. Additionally, the PAD may include positive or negative control regions. A negative control may be included in order to verify that the PAD has not become contaminated during storage or use or that the solvent used to develop the colors does not interfere with a color generating reaction. A positive control may be included to show that the reagents in a test lane are still viable, or it may be used as a standard for the image analysis software as disclosed hereinbelow. The PAD may also contain assay regions whose only function is to demonstrate that the user has complied with instructions for correct use of the PADs, or assay regions whose function is to demonstrate that the PAD is an authentic device and not a counterfeit.

Information Identification Zone

The paper analytical device contains at least one electronically readable information zone, which provides information necessary for determining the outcome of the test performed on the PAD based on images obtained by a camera device. The information zone typically includes appropriate information that is electrically readable per se or after being photographed or otherwise imaged electronically. Such information may include an identification tag such as a two-dimensional bar code (e.g., a QR code), color standards, and/or fiducial or alignment marks.

Each PAD can be imprinted with a two-dimensional barcode such as a Quick Response (QR) barcode that contains the type and serial number of the PAD so that a PAD test can be uniquely identified and the necessary color processing steps to perform the test can be automatically determined, which provides a simple and inexpensive way to uniquely identify the PAD, in addition to providing pertinent information for perspective distortion correction and subsequent color analysis. Depending on the application, other information can also be encoded in the two-dimensional code image. A key task of the image analysis software is the perspective correction or transformation of distorted images, which transforms an image captured at an unknown standoff and optical axis position to a canonical coordinate system in which regions to be analyzed for subsequent color characterization are expressed. The origin and basis vectors for this coordinate system can be automatically calculated from the position of "finder marks" or fiducial marks on the QR code. In some embodiments, each PAD may also contain one or more additional fiducial markers such as "finder squares" or rectifiers to eliminate angle and 3D distortions of the PAD's photographed image. The identification zone can be placed anywhere on the PAD. Preferably, the identification zone can be printed on the PAD prior to application of hydrophobic regions and the identification zone is located on an upper corner of the PAD. Typically, this is included on the substrate that is sealed in a separate compartment of the lamination. Depending upon the material of the substrate, it can also be provided in the compartment with the vessels provided that it is visible. It also can be provided on an outer portion of the lamination. A skilled artisan can best determine where to locate this component for optimum use in calibration and analysis of the information that is provided in the assaying regions during testing, as well as to facilitate registration and orientation of the PAD.

Color Calibration Zone

In analyzing a PAD, the color content of specific regions of the PAD will be analyzed to automatically determine the test result. This removes human subjectivity in color interpretation. However, PAD images may be captured under different ambient lighting conditions and their global effect on PAD color distributions must be suppressed. Thus, it is important to perform color calibration using the color calibration zone on the PAD, which consists of different colored sub-regions, including a white region and a black region. Image analysis software can be used to compare the extracted colors in the PAD image's color calibration zone to known values to identify the specific color correction methods needed. One such method is white balancing, in which the overall brightness of the image is adjusted to force the white square in the PAD image to have a pure white color value. The calibration zone can be in any suitable shape, including rectangles, squares, circles, or triangles. The sub-regions can be in any suitable shape, including rectangles, squares, circles or triangles. Preferably, the color calibration zone is a rectangle region and the sub-regions are different colored squares. The color calibration zone can be printed onto the PAD prior to or after application of hydrophobic regions. The calibration zone can be placed anywhere on the PAD. Preferably, the calibration zone is printed on the PAD prior to application of hydrophobic regions and is located on an upper corner of the PAD.

In the preferred embodiment, the PAD of the invention comprises one information zone having a color calibration zone, another information zone having multiple fiducial marks, and yet another information zone comprising a QR code or other identification tag.

The method further comprises providing a camera device, capturing an image of the PAD that has reacted with the composition using the camera device, and providing an image analysis software capable of using information provided by the information zone and the image of the test result in order to identify and quantify a colorimetric change within the assay region of the paper analytical device shown in the captured image. In the preferred embodiment of the method of the invention, the capture image contains a two-dimensional bar code such as a QR code and one or more fiducial markers. The image software identifies the QR code region, separates the image of the PAD's assay regions from background present in the picture, scales, rotates, and performs geometrical transformations on the captured PAD image based on the QR code and the one or more fiducial markers, aligns the PAD assay regions with stored images in the database, reads test results from pre-specified locations in the stored assay regions, and classifies the test results. The method of the invention further comprises compiling a database of the captured images of the paper analytical devices and the computed test outcomes, wherein the two-dimensional barcode is a QR code that allows for automated identification of a specific PAD including the PAD-type, serial number and fabrication date.

In one embodiment, the image analysis software is provided on the camera device for processing the captured image in situ. Alternatively, the image analysis software may be provided on a network server such that the captured image is processed by sending the picture to the network server that performs the analysis and transmits the results back to the camera device.

Controls

The hydrophobic regions can also define control regions within the hydrophilic paper medium. For example, a timer region may be included in order to alert the user when the test has completed. The time region may comprise a colorimetric indicator. Additionally, the PAD may include positive or negative control regions. A negative control may be included in order to verify the purity of the reaction solvent. A positive control may be included in order to verify the presence (or absence) of the chemical to be detected. The control substrates, if any, may be included in the paper medium at the time the other colorimetric reagents are added to the paper medium. The PAD may also contain hydrophilic regions for titrations and/or reverse titrations, as well as user compliance lanes for improving the accuracy of the quantitative analysis of the chemicals.

Kits

The PADs may be packaged in kits providing a user with all of the materials necessary for using the PAD. For example, the kit may contain a solvent (such as deionized water or ethanol), a plastic micropipette, weighing paper, and a cotton swab. Instructions may be provided in hard copy, accessible via a link to a website or mobile application, accessible via a QR code or any combination thereof (including any equivalent and complementary instruction formats). The PADs comprising test reagents may be subjected to degradation due to temperature, light, or moisture which may affect the accuracy of the tests performed. As a result, the PADs may be individually packaged and sealed in light- and moisture-resistant packets. Additionally, the packets may be packaged with a desiccant in order to maintain a specific moisture level, and remove excess moisture. Another embodiment of the invention is a kit for detecting the presence/absence of a chemical and/or a chemical functional group in a composition, quantifying a chemical in a composition, or measuring the relative amounts of two materials present in a composition. Typically, the kit includes a PAD as disclosed herein; a solvent sufficient to saturate the paper assay device; and instructions for detecting the presence/absence of a chemical and/or a chemical functional group in a composition, quantifying a chemical in a composition, or measuring the relative amounts of two materials present in a composition. Preferably, the solvent is one that is sufficient to dissolve or suspend the composition containing the chemical and/or the chemical functional group to be analyzed. Typically, the kit contains a dish to hold the solvent and a spatula swab, or pipette for applying the composition onto the PAD.

Figure 4:
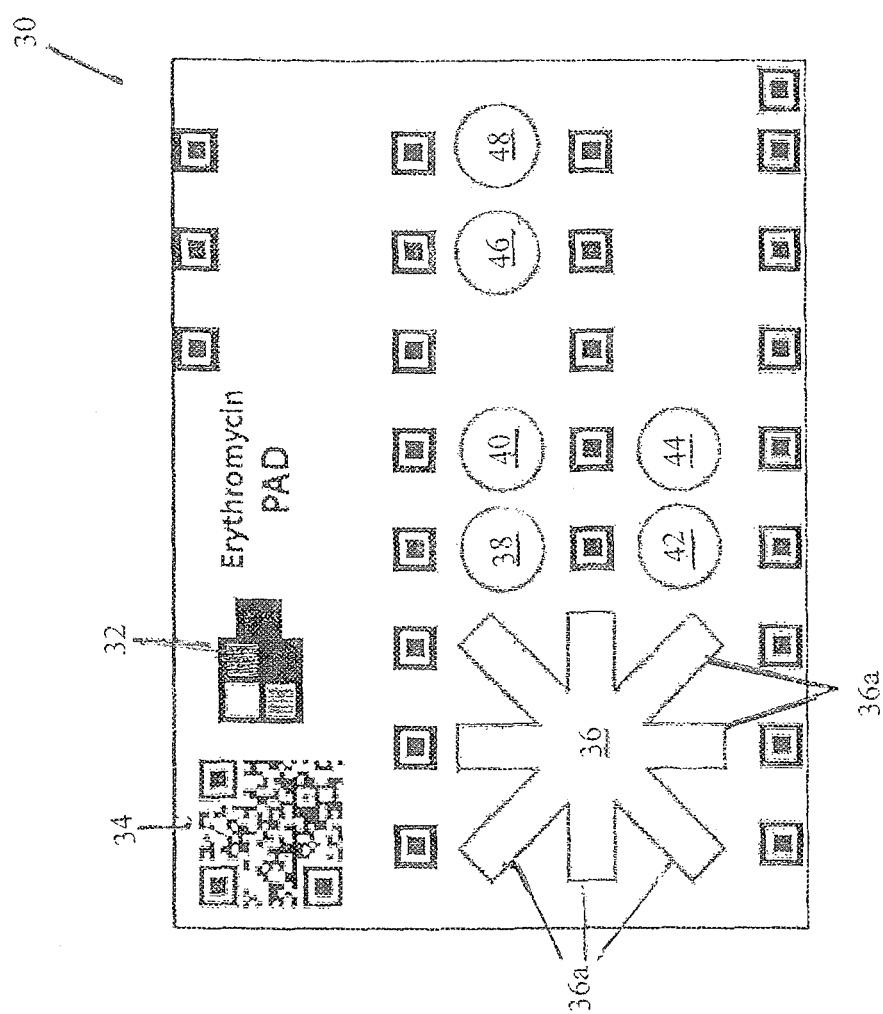
FIG. 4 shows an exemplary Erythromycin PAD.

The exemplary "cut and paste" devices 10 and 10' described hereinabove are conducive for use with a variety of PAD embodiments in a kit. FIG. 4, for example, shows an exemplary embodiment of an Erythromycin PAD 30 comprising a color calibration zone 32, an identification zone 34, reaction areas as well as a timer region. PAD 30 includes a "red flag" wheel 36 having a plurality of spokes 36a wherein each spoke is customizable with different chemicals to test for unique excipients and counterfeiting agents. The specific type of chemical in each spoke can be selected depending upon where the test is being conducted as well as to anticipate the types of counterfeit drugs that may be in use in such areas. If a spoke turns a different color when activated, such color change is indicative of the presence of a counterfeiting agent. Reaction areas 38, 40, 42, 44, 46 and 48 work in concert to perform a quantitative and qualitative assessment of the active ingredient and possible counterfeiting agents. In an exemplary PAD 30, HCl and Bromocresol green at area 38 works in conjunction with HCl and Methyl yellow at area 40 to help determine the concentration of Erythromycin. Ninhydrin at area 42 detects counterfeiting agents with primary or secondary amines. Sodium nitroprusside-acetylaldehyde at area 44 detects the presence of amines and counterfeiting agents. At area 46, phenol treated paper over a capillary containing sulfuric acid detects and differentiates between certain reducing sugars when activated colorimetrically. At area 48, ferric iron in glacial acetic acid and concentrated sulfuric acid, contained in a glass capillary under glass fiber paper, detects the presence of macrolide rings when activated. It is understood that testing is not constrained by the examples disclosed herein. For instance, wheel 36 and spokes 36a thereof may be customizable along with the reaction areas to proactively combat changes in counterfeiting efforts. As counterfeiters recognize the testing patters of a PAD 30 and alter their products according, PAD 30 can be customized with alternative testing reagents in anticipation of the alteration of counterfeit products.

Lastly, the color changes of the PAD regions of interest are identified to determine a qualitative or qualitative test result. While the precise amount of active agent may not be identified, the brightness or intensity of the assaying region can provide some indication of the relative amount of active agent that is present in the product tested.

EXAMPLE

An illustration of the invention and a comparison of its advantages over other devices appears below.

The Problem:

During the development of the Erythromycin PAD, it became necessary to create a new method for PAD fabrication. The paper had to be unadulterated, and the PAD had to be compatible with organic solvents. It was also necessary to develop a method of stabilizing certain reagents for long term storage. To this end, the Cut & Paste/Capillary Method was developed.

The PADs are developed as business-card sized testing systems that can help determine the authenticity of a suspicious pharmaceutical. Paper, or another absorbant material, is impregnated with a colorimetric reagent(s) that will indicate when a particular chemical or functional group is present.

The assay regions of the PAD were produced in a number of ways that are known to one skilled in the art:

SU-8 Method:

The paper medium is saturated with a crosslinking photoresist and then exposed to UV radiation in a pattern, creating hydrophobic and hydrophilic zones thereby.

Wax Method:

A modified inkjet printer places hydrophobic barriers of black wax to create lanes. The PAD is then heated to ensure full permeation through the paper.

Cut & Paste/Capillary Method:

The multilayer cut and paste design uses parafilm to attach unadulterated test strips to a laminate backing (e.g., as shown and described herein with respect to FIG. 1). Capillaries are loaded with unstable or corrosive reagents that are built into the PAD so that they can be broken on-site to release the reagent (e.g., as shown and described herein with respect to FIGS. 3 and 3A).

Cost Comparison:

Cost of reagents and labor were assumed to be approximately equal and therefore ignored for the purposes of this analysis.

TABLE 1

SU-8:

Paper: $0.07 per PAD (4,800 PADs per 100 sheet pack - $290.00)
SU-8 photo resist: $1.315 per PAD
Total: $1.36 per PAD Wax:

Paper: $0.09 per PAD (3,200 PADs per 100 sheet pack - $290.00)
Monochrome Wax Printing: $0.03 per PAD
Total: $0.12 per PAD Cut & Paste:

Paper: $0.013 per PAD (18,728 PADs per 100 sheet pack - $290.00)
Laminate: $0.032 per PAD (450 PADS per 50 sheet pack - $14.85)
Printer Paper: $0.002 per PAD (4,500 PADs per 500 sheets pack - $10.00)
Parafilm: $0.034 per PAD (2,602 PADs per 250' x 4" pack - $89.10)
Total: $0.08 per PAD

TABLE 2

Observed Assets and Limitations

|  | SU-8 | Wax | Cut & Paste/Capillary |
|---|---|---|---|
| ASSETS | Precise lane control | Somewhat biodegradable | Very versatile |
|  | Rigid | Unadulterated paper | Can use multiple types of absorbant material |
|  | Insensitive to most temperature conditions |  | Precise lane control |
|  |  |  | Unadulterated paper |
|  |  |  | Rigid |
|  |  |  | Can be easily scaled up |
|  |  |  | Needs less packaging |
|  |  |  | Insensitive to most temperature conditions |
|  |  |  | Lowest cost |
| LIMITATIONS | Cannot be used for acid sensitive analytes | Cannot use organic solvents | Not biodegradable |
|  | One type of paper | One type of paper | More involved fabrication method |

TABLE 2-continued

Observed Assets and Limitations

| SU-8 | Wax | Cut & Paste/Capillary |
|---|---|---|
| Not biodegradable | Lack of precise lane control | |
| Adulterated paper | Not rigid ("floppy") | |
| More involved fabrication method | Needs significant packaging | |
| More difficult to scale up | Sensitive to very warm temperature conditions | |
| Needs significant packaging | | |
| Relatively higher cost | | |

For the sake of brevity, it should be understood that certain structures and functionality, or aspects thereof, of embodiments of the presently disclosed invention that are evident from the illustrations of the figures have not been necessarily restated herein. Also, additional features relating to the use of the present invention can be found in U.S. patent application Ser. No. 13/566,915, filed Aug. 3, 2012, the entire disclosure of which is expressly incorporated herein by reference herein. For example, a combination PAD can be made which includes assaying regions in which the suspect substance is placed thereon, one or more vessels are provided for activating the PAD and allowing the suspect substance and reagent to chemically react yielding a color change, and then analyzing the PAD results either visually or electronically with the use of a camera. Such as PAD may also include a combination approach where dry reagents are included on other assaying regions adjacent to by spaced from the vessels and paper assaying regions. Therefore, some of the assaying regions are in lanes that involve only dry reagents, and others are adjacent to the vessels that contain the wet reagents, and some can even be combinations of dry and wet reagents. The dry reagents would be activated by the addition of a solvent, typically, water, which can be applied by a dropper or small cup to wet the assaying of regions that contain the dry reagent and sample to be tested while the breaking of the vessels activates the other assaying regions of the PAD. The wet and dry lanes can alternate or the PAD can be arranged with the dry lanes on, e.g., the right side of the PAD with the wet lanes and tubes arranged on the left side of the PAD. With this arrangement, only the right side of the PAD needs to be activated by adding water while the left side would be activated by simply breaking the vessels. And another arrangement would be to place the wet lanes in an upper part of the PAD and the dry lanes in a lower part of the PAD. This would allow the user to simply stand the PAD in a shallow dish of water so that the dry lanes canoe wet by capillary action after the vessels in the upper part of the PAD and fractured to allow the wet reagents to move on the assaying regions. And where the assaying regions need activation by both the wet reagents and water, they would be arranged in a particular location on the PAD where both liquids can be applied. Of course other arrangements are possible as would be understood by skilled artisans.

Therefore, it is to be understood that the presently disclosed invention is not to be limited to the exact configurations as illustrated and described herein. To those of ordinary skill in the art, one or more inventions will be understood to be contemplated from the present application. Accordingly, all expedient modifications readily attainable by one of ordinary skill in the art from the disclosure set forth herein, or by routine experimentation there from, are deemed to be within the spirit and scope of the invention as defined by the appended claims.

What is claimed is:

1. A multilayer paper analytical device for detection of a low quality pharmaceutical product or dietary supplement, comprising:
   one or more assay regions;
   one or more vessels each having a wall that houses one or more reagents in registry with at least one assay region for which testing for a chemical component is desired; and
   a non-chemically interfering binder agent disposed between the assay regions and vessels;
   wherein the vessels are arranged to be adjacent to the assaying regions with the binding agent providing a fluid path such that rupture of a vessel wall establishes fluid communication between the one or more reagents released by the ruptured vessel wall and the corresponding assay region along the fluid path;
   a hydrophobic material in the form of a sheet that is adjacent each vessel and that has openings that forms part of the fluid path for each vessel;
   wherein each assay region is configured to receive a sample of a suspected a low quality pharmaceutical product or dietary supplement such that, after activation of the device by rupturing of a vessel wall in registry with the assay region, the reagent wets the assaying region for reaction with the sample.

2. The device of claim 1, wherein the at least one vessel is fabricated from a rupturable material.

3. The device of claim 1, wherein the binder agent is parafilm, the assaying region comprises a hydrophilic substrate, the assaying region is adhered to the plastic sheet of the hydrophobic material by the parafilm, and the parafilm has an opening which is in alignment with the opening of the hydrophobic material sheet to assist in forming the fluid path between the vessel and the assaying region.

4. The device of claim 1, wherein the hydrophobic material is part of a lamination that surrounds the one or more vessels to contain therein any fluid which does not flow to the assaying region and the assaying regions are attached to an outer surface of the plastic sheet.

5. The device of claim 1, further comprising an informational substrate that is associated with the PAD in a visible position thereon.

6. The device of claim 5, wherein the informational substrate includes an information identification zone or a color calibration zone that includes reference colors to assist in processing of the color information obtained from the assay regions after activation of the device to more accurately detect the at least two chemical components, or both zones.

7. The device of claim 5, wherein the informational substrate includes at least one optically readable information zone that, after activation of the device, provides color information necessary for detection of the at least two chemical components, and wherein the least one optically readable information zone comprises alignment references for transforming or correcting a captured image of the paper analytical device to facilitate analysis and processing of the color information to more accurately detect the at least two chemical components.

8. The device of claim 7, wherein the alignment references include a plurality of fiducial markers for orienting the captured image.

9. The device of claim 1, further comprising at least one or both of an identification tag and a timer region that indicates when the test is completed.

10. The device of claim 5, wherein the informational substrate is included in the lamination and isolated from the vessels.

11. The device of claim 1, which includes one or more additional assaying regions that contain dry reagents that are activated by the separate addition of a solvent to conduct further testing of a sample of the product.

12. A method for detection of a low quality pharmaceutical or dietary supplement product, which comprises:
   providing a multilayer analytical device according to claim 1;
   disposing the pharmaceutical product to be analyzed into assay regions;
   activating the device in a manner such that the reagents contact the product to be analyzed in the assay regions to provide color information; and
   analyzing the color information to detect the presence or absence of certain chemical components of the pharmaceutical or dietary supplement product.

13. The method of claim 12, wherein the pharmaceutical or dietary supplement product to be analyzed is disposed upon the assay regions by depositing the product onto the device or by applying a dilution containing the product onto the device;
   wherein the activating of the device includes rupturing of the vessel wall sufficiently to enable release of the reagents therein to establish communication with the assay regions; and
   wherein disposing the product into the assay region and activating the device cause a color change that can be analyzed to detect the presence or absence of the chemical components of the product.

14. The method of claim 12, wherein the device further includes a color calibration zone that includes reference colors to assist in processing of the color information obtained from the assay regions after activation of the device to more accurately detect the at least two chemical components, and the method further comprises automating the color analyzing by:
   capturing an image of the device using a camera device; and
   providing image analysis software capable of recognizing and quantifying a color change within the assay regions of the device that is shown in the captured image.

15. The method of claim 12, which further comprises:
   repeating the detection for a plurality of pharmaceutical and dietary supplement products; and
   compiling a database of the captured images of the analytical devices, including time stamping and geo-tagging of the captured images.

16. The method of claim 12, wherein the chemical components to be detected include an active ingredient and an excipient, and:
   the presence of one of the chemical components determines that the pharmaceutical or dietary supplement product contains an insufficient amount of active ingredient;
   the absence of one of the chemical components determines that the product does not contain an appropriate active ingredient;
   the absence of one of the chemical components determines that the product does not contain an appropriate excipient; or
   the presence of one of the chemical components determines that the product contains an inappropriate excipient.

17. The method of claim 12, wherein the chemical components to be detected include an active ingredient and an excipient, wherein the active ingredient includes at least one of an anti-malarial, antibiotic, anti-parasitic, cox-inhibitor, analgesic, antipyretic, anti-viral, anti-cancer and dietary supplement compound and wherein the color information determines whether an inappropriate combination of active ingredient and excipient is present, indicative of a low quality pharmaceutical or dietary supplement product.

18. The method of claim 12, wherein the chemical components to be detected include an active ingredient and an excipient, wherein the active ingredient includes at least one of a pharmaceutical or dietary supplement compound and wherein the color information determines whether an inappropriate combination of active ingredient and excipient is present, indicative of a low quality pharmaceutical or dietary supplement product.

19. A kit for detection of a low quality pharmaceutical or dietary supplement product, the kit comprising:
   a multilayer analytical device according to claim 1;
   instructions for using the kit; and
   a solvent that is present in an amount sufficient to dilute the product to be analyzed to an analyzable concentration.

* * * * *